(12) United States Patent
Chambaud et al.

(10) Patent No.: US 9,408,878 B2
(45) Date of Patent: Aug. 9, 2016

(54) *LACTOCOCCUS LACTIS* STRAINS FOR USE IN IMPROVING DIGESTIVE CONDITION

(75) Inventors: Isabelle Chambaud, Issy les Moulineaux (FR); Biliana Lesic, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 404 days.

(21) Appl. No.: 13/994,376

(22) PCT Filed: Dec. 17, 2010

(86) PCT No.: PCT/IB2010/055913
§ 371 (c)(1),
(2), (4) Date: Aug. 21, 2013

(87) PCT Pub. No.: WO2012/080789
PCT Pub. Date: Jun. 21, 2012

(65) Prior Publication Data
US 2013/0336944 A1    Dec. 19, 2013

(51) Int. Cl.
*A61K 49/04* (2006.01)
*C12N 1/12* (2006.01)
*A61K 35/742* (2015.01)
*A23C 9/12* (2006.01)
*A61K 35/74* (2015.01)
*C12N 1/20* (2006.01)

(52) U.S. Cl.
CPC .............. *A61K 35/742* (2013.01); *A23C 9/12* (2013.01); *A61K 35/74* (2013.01); *C12N 1/20* (2013.01)

(58) Field of Classification Search
None
See application file for complete search history.

(56) References Cited

U.S. PATENT DOCUMENTS

2007/0172547 A1 *   7/2007   Kume et al. .................... 426/36

FOREIGN PATENT DOCUMENTS

| WO | 97/16529 | 5/1997 |
| WO | WO 97/16529 A1 * | 5/1997 |
| WO | 2004/103082 | 12/2004 |

OTHER PUBLICATIONS

Veiga, *Bifidobacterium animalis* Subsp. *lactis* Fermented Milk Product Reduces Inflammation by Altering a Niche for Colitogenic Microbes, Proceedings of the National Academy of Sciences of the United States of America, 107, pp. 18132-18137, 2010.

* cited by examiner

*Primary Examiner* — Jennifer McDonald
*Assistant Examiner* — Qing Xu
(74) *Attorney, Agent, or Firm* — Morgan, Lewis & Bockius LLP

(57) ABSTRACT

The present invention concerns strains of *Lactococcus lactis* capable of inhibiting the growth of a pathogenic microorganism and/or improving the intestinal epithelial barrier integrity. These strains are suitable for use in the treatment or prevention of a digestive disorder.

8 Claims, No Drawings

LACTOCOCCUS LACTIS STRAINS FOR USE IN IMPROVING DIGESTIVE CONDITION

The present invention relates to compositions comprising a lactic acid bacteria for use in improving a digestive condition. Particularly, such compositions comprise a *Lactococcus lactis* strain suitable to treat and/or prevent digestive disorders.

Gastrointestinal infections are extremely common around the world. In the vast majority of affected people a full recovery occurs rapidly. However, a substantial proportion of patients suffering from gastroenteritis develop long standing gastrointestinal symptoms such as Irritable Bowel Syndrome (IBS). Indeed, it is estimated that 3.7 to 36% of individuals develop IBS after bacterial or viral gastroenteritis (Spiller and Garsed, 2009).

Gastrointestinal infections are also among the most frequent causes of diarrhoea. In severe cases, the infection causing the diarrhoea may further cause gastric inflammation.

Gastrointestinal infections also include Crohn's disease (CD) and ulcerative colitis (UC), which are collectively referred to as Inflammatory Bowel Diseases (IBD).

Irritable Bowel Syndrome (IBS)

IBS is a chronic functional disorder of the colon that is characterized by diarrhea or constipation, abdominal pain, abdominal bloating, and passage of mucus in the stool.

Inflammation and infection are thought to play a role in the generation of IBS (Ohman and Simren, 2010). Enterobacteriaceae family was observed to be more abundant in IBS subjects compared to healthy subjects (Si et al., 2004). However, this observation was not repeated in others studies (Malinen et al., 2005) indicating that in case where Enterobacteriaceae bacteria play a role in the pathogenesis of IBS, it is not the only factor. Besides, it has been shown that IBS subjects harbor more enteroaggregative *Escherichia coli* (i.e., pathogenic strains of *Escherichia coli*) than healthy subjects (Sobieszczanska et al., 2006).

Whereas there is only association between amount of Enterobacteriaceae and subgroup of IBS, there is increasing evidence that members of Enterobacteriaceae family can trigger IBS in the case of post-infectious IBS (PI-IBS) (Ji et al., 2005; Marshall et al., 2010 and Thabane et al., 2010). In these studies, it was shown that subjects suffering from gastroenteritis caused by Enterobacteriaceae bacteria (*Escherichia coli, Campylobacter, Shigella*) presented more risk to have IBS.

Since immune activation was recently suggested as a putative pathophysiology cause of IBS, investigators started to assess the use of anti-inflammatory agents as a treatment of IBS (Camilleri, 2010). For instance, the anti-inflammatory agent Mesalamine showed very promising results in IBS subjects (Corinaldesi et al., 2009). In this study, it was shown that Mesalamine alleviated IBS symptoms improving the general well-being.

Further, probiotics, in particular strains of lactic acid bacteria, have been reported to be beneficial in the treatment and/or prevention of IBS. Examples of such strains are disclosed in International Applications WO 2007/036230, WO 03/010297 and WO 2009/080800.

Post Infectious Irritable Bowel Syndrome (PI-IBS)

PI-IBS is a subgroup of Irritable Bowel Syndrome that one develops after a gastrointestinal infection.

PI-IBS has been mainly reported in Europe, particularly in UK. Nonetheless, two recent studies, one from China and one from Korea, have reported that PI-IBS also occurs in Eastern countries with a prevalence similar to that found in the West.

Pathogenic bacteria have been identified in most studies as etiological factors involved in the development of PI-IBS. Enterobacteriacae such as *Salmonella, Shigella* and *Campylobacter* were among the most frequently isolated bacteria. Potentially other bacteria causing gastroenteritis could be involved such as *Listeria* or pathogenic *E. coli*. Recent studies indicate that other infectious agents including viruses (e.g., rotavirus, adenovirus, calcivirus) and parasites (*Giardia lamblia, Blastocystis hominis*) may also be involved. An hypothesis is that reduction of incidence of intestinal infections in general might reduce incidence of PI-IBS and possibly severity of PI-IBS symptoms.

The underlying mechanism of PI-IBS has not been clearly identified. Particular attention has been paid to the role of ongoing mild inflammation. Spiller and Garsed (2009) found increased numbers of intra-epithelial lymphocytes, lamina propria T lymphocytes, mast cells and calprotectin-positive macrophages that failed to decline in patients who develop PI-IBS. Few probiotic strains have been shown to have anti-inflammatory properties.

The epithelial lining of the intestine, comprising epithelial cells and tight junctions, is semi-permeable, allows the passage of small particles and is involved in the maintenance of mucosal barrier function. In vitro and in vivo studies suggest that an activated intestinal immune system in PI-IBS is the result of a raised local antigen exposure associated with an increased permeability of the intestinal epithelial layer. Patients with PI-IBS, have increased permeability compared with healthy subjects. The decrease of intestinal permeability might directly benefit PI-IBS symptoms. While several studies have shown that several strains of *Lactobacilli* species are able to increase epithelial barrier integrity, there is no direct evidence that *L. lactis* strains have similar properties. In contrast there are evidence that genetically modified *L. lactis* strains can be deleterious to the epithelium (Shao and Kaushal, 2004).

Inflammatory Bowel Disease (IBD)

IBD is either of two inflammatory diseases of the bowel: the Crohn's disease or the ulcerative colitis.

Crohn's disease and ulcerative colitis are chronic, idiopathic immune-mediated disorders, with genetic and environmental influences (factors), especially microbial influences. Crohn's disease is often associated with diarrhea, cramping, and loss of appetite and weight with local abscesses and scarring. Ulcerative colitis is also associated with diarrhea but with discharge of mucus and blood, cramping abdominal pain, and inflammation and edema of the mucous membrane with patches of ulceration. Crohn's disease and ulcerative colitis preferentially occur in areas with the highest concentrations of predominantly anaerobic bacteria in the distal ileum and colon. Serologic responses to microbial antigens are present in 80% of Crohn's disease patients and high titers of antibacterial serologies are associated with severe disease (Mow et al., 2004).

A continuing controversy in Crohn's disease is whether a pathogen is responsible for the chronic relapsing nature of the inflammatory response. Considerable recent evidence implicates functionally abnormal *E. coli* strains (belonging to Enterobacteriaceae) in the pathogenesis of Crohn's disease (Sartor, 2008). Adherent/invasive *E. coli* (AIEC) adhere to and invade epithelial cells and persist within intestinal epithelial cells and macrophages (Darfeuille-Michaud et al., 1998). The virulence factors and molecular mechanisms that promote epithelial adherence, invasion and persistence are being elucidated by in vitro studies (Darfeuille-Michaud et al., 1998 and Baumgart et al., 2007).

An active area of investigation in IBD assesses the possibility of dysbiosis, which is abnormal microbial composition or function, as a cause of chronic intestinal inflammation.

Dysbiosis can induce intestinal inflammation by several mechanisms (Sartor, 2009). Defective production of butyrate and other short chain fatty acids could profoundly affect colonic epithelial function and mucosal barrier characteristics. The relative balance of beneficial and detrimental bacteria may be crucial to induction of inflammation versus mucosal homeostasis. The ability of enteric microbiota to produce toxic metabolites may be relevant to the pathogenesis of ulcerative colitis. Intestinal bacteria can also produce reactive oxygen species that can cause tissue injury, particularly in a host with defective degradation of oxygen metabolites.

Several studies have documented marked alterations in the gut microbiota of patients with IBD (Peterson et al., 2008). It has been shown by molecular techniques, a contraction of certain bacterial population in IBD, especially clostridial subsets, and expansion of others, including Enterobacteriaceae (Sartor, 2009). Swidsinski et al. (2009) have noticed a higher level of Enterobacteriaceae in the microbiota of patients with CD and UC.

However, defining microbial features that are associated with or initiate IBD is complicated by host genetics, inflammation state and diet (Peterson et al., 2008). Designing prospective studies in human IBD to identify microbial communities that instigate inflammation has not been feasible, even in genetically susceptible populations.

Consequently, over the past few years, various murine models of chronic intestinal inflammation resembling IBD have been developed, and have provided information about IBD and microbiota deregulation. A variety of mouse models of IBD, including animals with genetically engineered defects in their immune system or mucus glycans, which have been conventionally—raised with a microbiota and then treated with antibiotics, or which have been raised germ-free and then colonized with a gut microbiota from a healthy donor, demonstrate that the presence of a microbiota is instrumental in eliciting pathology (Garrett et al., 2007; Kang et al., 2008 and Sartor, 2008). It is important to emphasize that although rodent models of colitis are generally dependent on the presence of gut microbes, not all microbes elicit disease (Kim et al., 2007). Animal model studies demonstrate that some bacterial strains are detrimental while others have protective effects, and many are neither aggressive nor beneficial (Sartor, 2009).

L. Glimcher's group has developed a robust mouse model of ulcerative colitis whose pathologic features and response to anti-TNF treatment closely resemble the human disease. They found that deficiency of a particular regulatory gene in the innate immune system (resulting from a double knock out of the genes T-bet and RAG2; named TRUC for T-bet RAG2 Ulcerative Colitis) resulted in aggressive, spontaneous, and communicable UC and increased susceptibility to colitis in immunologically intact hosts (Garrett et al., 2007).

These in vivo results are in accordance with clinical observation: *Klebsiella* and *Proteus* species are observed more frequently in the stool of patients with UC than healthy subjects (Dorofeyev et al., 2009). There are also numerous reports of elevated titers of antibodies against Enterobacteriaceae in patients with IBD (Cooper et al., 1988; Ibbotson et al., 1987 and Tiwana et al., 1998).

In conclusion, the balance of beneficial and detrimental bacterial species determines homeostasis versus inflammation. The implication of Enterobacteriaceae in these mechanisms was demonstrated. This balance can be manipulated in particular with probiotics to treat and prevent relapses of IBD.

It has also been shown that during active periods of IBD, the inflammation of the gastrointestinal tract causes an increased permeability of the epithelium, leading to deterioration of the epithelial barrier function (Madsen et al., 2001).

Use of anti-inflammatory chemicals (also called biologics) to treat Inflammatory Bowel Diseases increased lastly and are now currently use in IBD care by gastroenterologists and physicians (for review: Bosani et al., 2009). Alternatively, probiotics were used to alleviate IBD and anti-inflammatory mechanisms were suggested as mechanism of action (Vanderpool et al., 2008).

Further, increasing evidence suggests that some probiotic and commensal bacteria improve intestinal barrier impairment (decreasing the permeability) in vitro (Resta-Lenert and Barrett, 2006 and Miyauchi et al., 2008) and in vivo, and help in relieving IBS and IBD symptoms.

It appears from the foregoing that pathogens can cause gastrointestinal infections (including IBS, PI-IBS and IBD) and that compounds or probiotics having anti-pathogenic activity can prevent and/or treat these disorders. Further the integrity of the epithelial barrier associated to an anti-pathogenic activity can further avoid inflammations.

*Lactococcus lactis* bacteria are lactic acid bacteria commonly found in dairy products such as cheese or dairy fermented products (including yogurts). Some *Lactococcus lactis* bacteria have been described as having an activity against pathogenic Enterobacteriaceae such as *Salmonella enteritidis* and *Escherichia coli* (Olasupo et al., 2003; Gänzle et al., 1999).

The inventors have shown in vitro that two strains of *Lactococcus lactis* subsp. *lactis*, namely the strains DN 030 066 and DN 030 087, improve the epithelial barrier integrity compared to bacteria strains known for their anti-inflammatory properties, and further that the strain DN 030 066 has an excellent antimicrobial activity compared to strains known for their antimicrobial activity.

The strain DN 030 066 was deposited according to the Budapest Treaty at the CNCM (Collection Nationale de Cultures de Microorganisms, 25 Rue du Docteur Roux, Paris) on Oct. 24, 1995, with the numberI-1631. This strain is disclosed in International Application WO 97/16529.

The CNCM I-1631 strain has the following characteristics:
Morphology: Gram-positive microorganism, mainly diplococci of small size
Fermentation of the following sugars (results obtained on an API 50 CH strip—API MRS medium at 30° C. for 48 h): ribose, galactose, glucose, mannose, mannitol, N acetyl-glucosamine, amygdaline, arbutine, esculine, salicine, cellobiose, maltose, lactose, trehalose, amidon, β gentiobiose.

The strain DN 030 087 was deposited according to the Budapest Treaty at the CNCM (Collection Nationale de Cultures de Microorganisms, 25 Rue du Docteur Roux, Paris) on Feb. 19, 2002 with the number I-2807.

The CNCM I-2807 strain has the following characteristics:
Morphology: Gram-positive microorganism, mainly diplococci of small size
Fermentation of the following sugars (results obtained on an API 50 CH strip—API MRS medium at 37° C. for 72 h): ribose, galactose, glucose, mannose, mannitol, N acetyl-glucosamine, amygdaline, arbutine, esculine, salicine, cellobiose, maltose, lactose, melibiose, trehalose, amidon, β gentiobiose.

Accordingly, the present invention provides a *Lactococcus lactis* strain selected from the group consisting of the strains DN 030 066 (CNCM I-1631) and DN 030 087 (CNCM I-2807) for use in the treatment or prevention of a digestive disorder.

In an embodiment, said use is for inhibiting the growth of a pathogenic microorganism, preferably a pathogenic Enterobacteriaceae, and/or improving the intestinal epithelial barrier integrity.

Said pathogenic microorganism is preferably selected from the group consisting of the genus *Escherichia, Salmonella, Listeria, Campylobacter, Shigella, Proteus* (e.g., *P. mirabilis*) and *Klebsiella*, preferably from the group consisting of the species *E. coli, L. monocytogenes* and *S. enteritidis*.

Said digestive disorder can be in particular gastric or intestinal discomfort; gastric or intestinal infection; diarrhoea; constipation; IBS; PI-IBS or IBD (i.e., Crohn's disease and/or ulcerative colitis).

The present invention also provides a *Lactococcus lactis* mutant strain obtained from the strain DN 030 066 or the strain DN 030 087 by mutagenesis or genetic transformation thereof, for inhibiting the growth of a pathogenic microorganism, preferably a pathogenic Enterobacteriaceae, and/or improving the intestinal epithelial barrier integrity, in the treatment or prevention of a digestive disorder, as defined above.

Said *Lactococcus lactis* mutant strain is obtainable by mutating one or more endogenous gene(s) of the strain DN 030 066 or of the strain DN 030 087, for instance in order to modify some of its properties (e.g. its ability to ferment sugars, its resistance to acidity, its survival to transport in the gastrointestinal tract, or its post-acidification). It can also be a mutant strain resulting from the genetic transformation of the strain DN 030 066 or the strain DN 030 087 by one or more gene(s) of interest, for instance in order to confer to said strain additional physiological features.

Said strains can be used in the form of whole bacteria which may be dead or alive, preferably alive.

The present invention also provides a cell fraction or a metabolite obtained from the strain DN 030 066 or the strain DN 030 087, for inhibiting the growth of a pathogenic microorganism, preferably a pathogenic Enterobacteriaceae, and/or improving the intestinal epithelial barrier integrity, in the treatment or prevention of a digestive disorder, as defined above.

Said cell fraction can be for instance a cell-wall fraction, a cytoplasmic fraction, or a culture supernatant or a fraction thereof.

Said metabolite can be for instance short chain fatty acids, peptides (e.g., bacteriocins) and/or compounds produced during fermentation of the strains DN 030 066 or DN 030087.

The present invention also provides a composition comprising
- a *Lactococcus lactis* strain selected from the group consisting of the strains DN 030 066 (CNCM I-1631) and DN 030 087 (CNCM I-2807) as defined above, or
- a *Lactococcus lactis* mutant strain as defined above, or
- a cell fraction or a metabolite obtained from the strain DN 030 066 or the strain DN 030 087 as defined above, for inhibiting the growth of a pathogenic microorganism, preferably a pathogenic Enterobacteriaceae, and/or improving the intestinal epithelial barrier integrity, in the treatment or prevention of a digestive disorder, as defined above.

Said composition may comprises at least one other *Lactococcus lactis* strain different from the strains as defined above and/or at least one lactic acid bacteria of a species different from *Lactococcus lactis*, such as lactic acid bacteria of the genus *Lactobacillus* or *Bifidobacterium*.

Said composition can be in any form suitable for administration, in particular oral administration. This includes for instance solids, semi-solids, liquids, and powders. Liquid composition are generally preferred for easier administration, for instance as drinks.

Said composition may comprise $10^5$ to $10^{13}$ colony forming units (cfu), of at least one *L. lactis* strain or *L. lactis* mutant strain as defined above, preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Said composition can be a food product or a pharmaceutical product.

Said composition can also be a dairy product or a fermented product, preferably a fermented dairy product, such as a fermented milk product or fermented whey product.

The fermented product can be present in the form of a liquid or present in the form of a dry powder obtained by drying the fermented liquid.

The administration in the form of a fermented dairy product has the additional advantage of low lactose levels, which is further beneficial for improvement of a digestive disorder, as defined above.

Said fermented product can be a fresh product. A fresh product, which has not undergone severe heat treatment steps, has the advantage that bacterial strains present are in the living form.

Said fermented milk product can be yoghurt, or fermented milk in set, stirred or drinkable form or a cheese.

Said fermented product can also be a fermented vegetable product, such as fermented soy, cereals and/or fruits in set, stirred or drinkable forms.

In another embodiment, said composition is a baby food, an infant milk formula or an infant follow-on formula.

In another embodiment, said composition is a nutraceutical or a nutritional supplement.

Nutritional compositions of the invention also include food supplements, and functional food.

As used herein, a "food supplement" refers to a product made from compounds usually used in foodstuffs, but which is in the form of tablets, powder, capsules, portion or any other form usually not associated with aliments, and which has beneficial effects for one's health.

As used herein, a "functional food" is an aliment which also has beneficial effects for one's health. In particular, food supplements and functional food can have a physiological effect—protective or curative—against a disease, for example against a chronic disease.

Said composition is preferably intended for use in humans, including in particular infants, elderly subjects and subjects suffering from metabolic deregulation, for instance obese subjects, The present invention also provides a method for obtaining a *Lactococcus lactis* mutant strain capable of inhibiting the growth of a pathogenic microorganism, preferably a pathogenic Enterobacteriaceae, and/or improving the intestinal epithelial barrier integrity, comprising a step of mutagenesis or of genetic transformation of a *Lactococcus lactis* strain selected from the group consisting of the strains DN 030 066 (CNCM I-1631) and DN 030 087 (CNCM I-2807).

Methods of mutagenesis or genetic transformation of a *Lactococcus lactis* strain are well known by one of skilled in the art.

The present invention also provides a *Lactococcus lactis* strain, characterized in that it is the strain deposited with the CNCM under number I-2807.

Said strain is capable of inhibiting the growth of a pathogenic microorganism, preferably a pathogenic Enterobacteriaceae as defined above, and/or improving the intestinal epithelial barrier integrity.

The present invention also provides a composition comprising the *Lactococcus lactis* strain CNCM I-2807.

The present invention also provides the *Lactococcus lactis* strain CNCM I-2807 or a composition comprising said strain for use as a medicament.

The present invention also provides a method of treating or preventing a digestive disorder as defined above, in a subject in need thereof, comprising administering a *L. lactis* strain or composition as defined above to said subject.

In addition to the preceding features, the invention comprises other features which will emerge from the following description, which refers to examples illustrating the anti-pathogenic and Trans Epithelial Electrical Resistance (TEER) activity of the strains DN 030 066 and DN 030 087.

EXAMPLE 1

Evaluation of Anti-Pathogenic Activities of *L. Lactis* Strain DN 030 066

The antimicrobial activity against *Salmonella enteritidis* B1241, *Listeria* and pathogenic *E. coli* was determined in overlay assays. Three *Lactococcus lactis* strains were assessed in this test: the strain according to the present invention DN 030 066, the *Lactococcus lactis* subsp. *lactis* DSMZ 20729 and the *Lactococcus lactis* subsp. *cremoris* DSMZ 4645, previously described as bacteriocin producer strains (respectively nisin and lacticin) (Bartoloni et al., 2004 and Park et al., 2003).

*L. lactis* strains were transferred from the frozen stocks onto fresh agar plates using a stamp. The plates were grown overnight until visible colonies were seen. Then, a top agar containing brain-heart infusion broth and a dilution of the selected pathogens was poured onto the agar plates. Plates were incubated at 37° C. The next day, the diameters of the pathogen inhibition zones were measured.

Score 1 corresponds to a diameter between 1 and 3 mm, score 2 to a diameter between 4 and 6 mm, and score 3 to a diameter higher than 6 mm. Experiments were carried out in three different media: MRS (De Man Rogosa and Sharpe), Elliker and TGV (Tryptone-Glucose-Meat Extract). Each experiment was carried out independently in triplicate. The scores obtained for each medium were summed, to give, for each strain and each pathogen a specific score. Then, the scores obtained for each pathogen were summed, to give, for each strain, a global antimicrobial activity score. The results are shown in Table 1 below.

TABLE 1 antimicrobial activity of selected *Lactococcus lactis* strains.

| Species | Reference | *E. coli* | *L. monocytogenes* | *S. enteritidis* | Global antimicrobial score |
|---|---|---|---|---|---|
| *L. lactis* subsp. *lactis* DN 030 066 | PCT Application WO 97/16529 | 3 | 8 | 4 | 15 |
| *L. lactis* subsp. *lactis* DSMZ 20729 | Harris et al., 1992 | 3 | 7 | 2 | 2 |
| *L. lactis* subsp. *cremoris* DSMZ 4645 | Ryan et al., 1996 | 1 | 1 | 2 | 14 |

The above results show that the strain according to the present invention DN 030 066 has an antimicrobial activity superior to two *Lactococcus lactis* strains known for having anti-pathogenic activities.

Example 2

Teer Evaluations of *L. Lactis* Strains DN 030 066 and DN 030 087

The intestinal barrier integrity can be assessed by measuring the difference in potential observed between the apical and basal sides of a T84 cell monolayer. This experimental model is called the Trans Epithelial Electrical Resistance (TEER) (Hirotani et al., 2008).

Culture suspensions of different bacteria strains were washed with PBS. Then, the bacteria (100 cfu/cell) were added to the apical side of the T84 cell monolayers. 96 strains were tested in the assay, including 64 Bifidobacteria, 32 *Lactobacilli*, and 2 *Lactococcus lactis* (DN 030 0664 and DN 030 087). After 4 h and 6 h of incubation with the different bacteria, the TEER value was measured to assess the epithelial barrier function. All the experiments were performed three times independently and in triplicate. The value of the T84 cells at t=0 was set at 100%. The results for the 7 strains having the higher TEER value are shown in Table 2 below.

TABLE 2

TEER evaluation of selected bacteria strains

| Strains | Reference | TEER (%) at t = 4 h | TEER (%) at t = 6 h |
|---|---|---|---|
| *L. lactis* DN 030 066 | PCT Application WO 97/16529 | 110.90 | 113.94 |
| *L. lactis* DN 030 087 | Present invention | 108.54 | 102.79 |
| *L. rhamnosus* LGG ATCC 53103 | U.S. Pat. No. 4,839,281 | 96.94 | 101.43 |
| *L. acidophilus* LA1 | Link-Amster et al., 1994 | 93.29 | 100.78 |
| T84 cells (control) | | 100 | 100.49 |
| *Bifidobacterium longum* NCC2705 | PCT Application WO 2002/074798 | 99.83 | 94.87 |

TABLE 2-continued

TEER evaluation of selected bacteria strains

| Strains | Reference | TEER (%) at t = 4 h | TEER (%) at t = 6 h |
|---|---|---|---|
| Bifidobacterium longum W11 | Patent EP 1609852 | 100.81 | 87.68 |
| Bifidobacterium longum BB536 | Patent Application JP 2006081429 | 87.50 | 77.89 |

The above results show that the strains according to the present invention DN 030 0664 and DN 030 087 improve the epithelial barrier integrity compared to known strains (comprising strains having an anti-inflammatory activity).

REFERENCES

Bartoloni, A. et al. (2004) J Chemother. 16: 119-121.
Baumgart, M, et al. (2007) ISME J. 1: 403-418.
Bosani, M. et al. (2009) Biologics 3: 77-97.
Camilleri, M. (2010) Aliment Pharmacol Ther. 31: 35-46.
Cooper, R. et al. (1988) Br Med J. 296: 1432-1434.
Corinaldesi, R. et al. (2009) Aliment Pharmacol Ther. 30: 245-252.
Darfeuille-Michaud, A. et al. (1998) Gastroenterology 115: 1405-1413.
Dorofeyev, A. E. et al. (2009) Dig Dis. 27: 502-510.
Gänzle, M. G. et al. (1999) International journal of food 48: 37-50.
Garrett, W. S. et al. (2007) Cell 131: 33-45.
Harris, L. J. et al. (1992) Appl Environ Microbiol. 58: 1477-1483.
Hirotani, Y. et al. (2008) Yakugaku Zasshi 128: 1363-1368.
Ibbotson, J. P. et al. (1987) Eur J Clin Microbiol. 6: 286-290.
Ji, S. et al. J Gastroenterol Hepatol. 20: 381-386.
Kang, S. S. et al. (2008) PLoS Med. 5: e41.
Kim, S. C. et al. (2007) Inflamm Bowel Dis. 13: 1457-1466.
Link-Amster, H. et al. (1994) FEMS Immunol Med Microbiol. 10: 55-63.
Madsen, K. et al. (2001) Gastroenterology 121: 580-591.
Malinen, E. et al. (2005) Am. J. Gastroenterol. 100: 373-382.
Marshall, J. K. et al. (2010) Gut 59: 605-611.
Miyauchi, E. et al. (2009) J. Dairy Sci. 92: 2400-2408.
Mow, W. S. et al. (2004) Gastroenterology 126: 414-424.
Ohman, L. and Simren, M. (2010) Nat Rev Gastroenterol Hepatol. 7: 163-173.
Olasupo, N. A. et al. (2003) Letters in Applied Microbiology 36: 448-451.
Park, S. H. et al. (2003) Curr Microbiol. 46: 385-388.
Peterson, D. A. (2008) Cell Host Microbe 3: 417-427.
Resta-Lenert, S. and Barrett, K. E. (2006) Gastroenterology 130: 731-746.
Ryan, M. P. et al. (1996) Appl Environ Microbiol. 62: 612-619.
Sartor, R. B. (2008) Gastroenterology 134: 577-594.
Sartor, R. B. (2009) Nestle Nutr Workshop Ser Pediatr Program 64: 121-132; discussion 132-127, 251-127.
Shao, J. and Kaushal G. (2004) Int J Pharm. 286: 117-124.
Si, J. M. et al. (2004) World J Gastroenterol. 10: 1802-1805.
Sobieszczanska, B. M. et al. (2006) J Med. Microbiol. 55: 325-330.
Spiller, R. and Garsed, K. (2009) Gastroenterology 136: 1979-1988.
Swidsinski, A. et al. (2009) J Physiol Pharmacol. Suppl 6: 61-71.
Thabane, M. et al. (2010) Am J Gastroenterol. 105: 933-939.
Tiwana, H. et al. (1998) Br J Rheumatol. 37: 525-531.
Vanderpool, C. et al. (2008) Inflamm Bowel Dis. 14: 1585-1596.

The invention claimed is:

1. A method of treating or decreasing the probability for developing an intestinal disorder in a subject in need thereof comprising administering to the subject a *Lactococcus lactis* strain selected from the group consisting of the strains DN 030 066 (CNCM I-1631) and DN 030 087 (CNCM I-2807) in an amount effective to treat or decrease the probability for developing the intestinal disorder.

2. The method according to claim 1, wherein the effective amount of *Lactococcus lactis* strain inhibits growth of a pathogenic microorganism and/or improves intestinal epithelial barrier integrity.

3. The method according claim 2, wherein said pathogenic microorganism is a pathogenic Enterobacteriaceae.

4. The method according to claim 1, wherein said intestinal disorder is selected from the group consisting of diarrhoea, constipation, Irritable Bowel Syndrome (IBS), Post-Infectious Irritable Bowel Syndrom (PI-IBS) and Inflammatory Bowel Disease (IBD).

5. A method of treating or decreasing the probability of an intestinal disorder in a subject in need thereof comprising administering to the subject a cell fraction or a metabolite obtained from strain DN 030 066 or strain DN 030 087, in an amount effective to inhibit growth of a pathogenic microorganism and/or improve intestinal epithelial barrier integrity.

6. The method according to claim 5, wherein said metabolite is selected from the group consisting of short-chain fatty acids, peptides and other compounds produced during fermentation of the strain DN 030 087.

7. A fermented milk food product composition comprising a *Lactococcus lactis* strain deposited with the CNCM (Collection Nationale De Cultures De Microorganismes) under the accession number I-2807.

8. The fermented milk food product composition of claim 7, wherein *Lactococcus lactis* CNCM 1-2807 has an amount of at least $10^6$ cfu/ml.

* * * * *